United States Patent [19]

Wang et al.

[11] 4,073,745

[45] Feb. 14, 1978

[54] MULTICHROMOPHORIC BENZOTRIAZOLE ULTRAVIOLET STABILIZERS AND THEIR USE IN ORGANIC COMPOSITIONS

[75] Inventors: Richard H. S. Wang; Joseph S. Zannucci, both of Kingsport, Tenn.

[73] Assignee: Eastman Kodak Company, Rochester, N.Y.

[21] Appl. No.: 687,080

[22] Filed: May 14, 1976

Related U.S. Application Data

[62] Division of Ser. No. 502,333, Sept. 3, 1974, Pat. No. 3,981,884.

[51] Int. Cl.$^2$ .................. C09K 15/32; C09K 15/30; C08K 5/34
[52] U.S. Cl. .................................... 252/403; 106/176; 252/402; 260/45.8 NT
[58] Field of Search ................ 260/45.8 NT; 252/402, 252/403; 106/176

[56] References Cited

U.S. PATENT DOCUMENTS 3,766,205  10/1973  Heller et al. ..................... 260/308 B

FOREIGN PATENT DOCUMENTS 1,212,466  11/1970  United Kingdom ............. 260/308 B

*Primary Examiner*—H.S. Cockeram
*Attorney, Agent, or Firm*—J. Frederick Thomsen; Daniel B. Reece, III

[57] ABSTRACT

The invention relates to multichromophoric compounds which have been found to be effective ultraviolet stabilizers. The invention also relates to ultraviolet degradable organic compositions containing a stabilizing amount of the multichromophoric composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

34 Claims, No Drawings

MULTICHROMOPHORIC BENZOTRIAZOLE ULTRAVIOLET STABILIZERS AND THEIR USE IN ORGANIC COMPOSITIONS

This is a division of application Ser. No. 502,333 filed Sept. 3, 1974, now U.S. Pat. No. 3,981,884.

This invention relates to multichromophoric ultraviolet stabilizers and their use in organic compositions. More particularly, the invention relates to multichromophoric compositions and the stabilization of ultraviolet degradable organic compositions against deterioration resulting from the exposure to such radiations with such multichromophoric compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing multichromophoric compositions which are resistant to ultraviolet degradation.

It is a still further object of this invention to provide processes for improving the resistance of organic materials to deterioration and degradation of actinic radiation and especially ultraviolet radiation.

It is a still further object of this invention to provide compositions and processes for improving the resistance of organic materials to deterioration and degradation by actinic radiations, including short wave-length visible radiations.

Further objects and advantages of the invention will be apparent to those skilled in the art from the accompanying disclosure and claims.

In accordance with the present invention, multichromophoric compositions are provided which are useful as ultraviolet stabilizers or ultraviolet screening agents. These organic compositions contain at least one heterocyclic groups containing compositions connected to a hydroxybenzophenone. The multichromophoric compositions of the present invention have the following structure:

A—B—C wherein A is a group having the structure

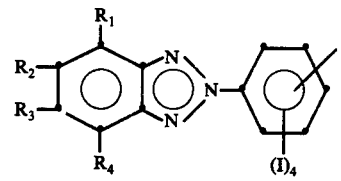

wherein
$R_1$, $R_2$, $R_3$ and $R_4$ are hydrogen, lower alkyl or substituted lower alkyl having 1 to 12 carbon atoms, cycloalkyl, substituted cycloalkyl, aryl or substituted aryl having 6 to 18 carbon atoms, lower alkylaryl, aryl-substituted-aryl, chloro, bromo, alkoxy, substituted amino, cyano, carboxy and the substitutents $R_1$ and $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$.

I is a substituent listed above for $R_1$, $R_2$, $R_3$ and $R_4$ and is present on all positions of the benzenoid ring, except the carbon atom attached to the N substituent and the carbon atom attached to the B group. The B connecting group is attached to the benzoid ring in the ortho, meta or para position from the carbon atom connected to the heterocyclic ring. The I substituents can all be one of the substituents listed above or different listed substituents;

wherein B is a linking group connecting A and C and can be alkylene, arylene, carbonyloxy, oxycarbonylalkyleneoxy, oxycarbonyl, alkyleneoxycarbonyloxy, oxyalkylenecarbonyloxy, oxycarbonyloxy, alkyleneoxy, oxyalkylene, alkyleneoxyalkyleneoxy, oxyalkylenearylenealkyleneoxy, thio, thioalkyleneoxy, sulfinyldioxy, oxy(alkoxy)-phosphinooxy, aminocarbonyl, N-alkylamino carbonyl, N-arylaminocarbonyl, aminocarbonylalkyleneoxy, N-alkylaminocarbonylalkyleneoxy, N-arylaminocarbonylalkyleneoxy, aminocarbonylamino, N-alkylaminocarbonylamino, N,N-dialkylaminocarbonyl, N-arylaminocarbonyl, N-alkylaminocarbonyl, N,N-diarylaminocarbonyl, amino, N-alkylamino, N-arylamino, N-alkylaminoalkyleneoxy, N-arylaminoalkyleneoxy, oxyalkyleneoxy, oxyaryleneoxy, alkyleneaminoalkylene, aryleneaminoarylene, aryleneaminoalkylene and alkyleneaminoarylene; and C is a hydroxybenzophenone group having the formula

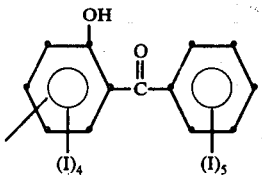

I is the same substituent as listed above and is present in all positions of the benzenoid rings except the carbon atom attached to the B group connecting the A and C moieties. The B connecting group is attached to the benzenoid ring in the ortho, meta or para position from the carbonyl group of the benzophenone. The I substituents can all be one of the substituents listed above or different listed substituents.

Suitable heterocyclic A groups having the structure

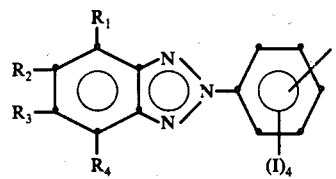

are for example substituted and unsubstituted benzotriazoles such as 4-(5-chloro-2H-benzotriazol-2-yl)phenyl, 4-(2H-benzotriazol-2-yl)phenyl, 4-(5-methoxy-2H-benzotriazol-2-yl)phenyl, 2,6-dimethyl-4-(2H-benzotriazol-2-yl)phenyl, 2,6-dimethyl-4-(5-chloro-2H-benzotriazol-2-yl)phenyl, 2-methyl-4-(2H-benzotriazol-2-yl)phenyl, 2-methyl-4-(5-chloro-2H-benzotriazol-2-yl)phenyl, 2-chloro-4-(2H-benzotriazol-2-yl)phenyl, 2,6-dichloro-4-(2H-benzotriazol-2-yl)phenyl, 2-chloro-4-(5-chloro-2H-benzotriazol-2-yl)phenyl, 2,6-dichloro-4-(5-chloro-2H-benzotriazol-2-yl)phenyl, 2,6-dimethyl-4-(5-methoxy-2H-benzotriazol-2-yl)phenyl, 2,6-dichloro-4-(5-methoxy-2H-benzotriazol-2-yl)phenyl, 2-chloro-4-(5-methoxy-2H-benzotriazol-2-yl)phenyl, 2-methyl-4-(5-methoxy-2H-benzotriazol-2-yl)phenyl, 2-phenyl-4-(2H-benzotriazol-2-yl)phenyl, 2-phenyl-4-(5-chloro-2H-benzotriazol-2-yl)phenyl, 2-phenyl-4-(5-methoxy-2H-benzotriazol-2-yl)phenyl, and the like.

Suitable B groups are for example alkylene, arylene, carbonyloxy, oxycarbonylalkylene such as oxycarbonylmethyleneoxy, oxycarbonylethyleneoxy, oxycarbonyl-1,4-butanediyloxy, oxycarbonyl, alkyleneoxycarbonyloxy such as methyleneoxycarbonyloxy, ethyleneoxycarbonyloxy, 1,4-butanediyloxycarbonyloxy, 1,5-pentanediyloxycarbonyloxy, oxycarbonyloxy, alkyleneoxy such as methyleneoxy, ethyleneoxy, 1,3-propanediyloxy and the like, alkyleneoxyalkyleneoxy such as methyleneoxymethyleneoxy, ethyleneoxyethyleneoxy, methyleneoxyethyleneoxy, ethyleneoxymethyleneoxy and the like, oxyalkyleneoxy such as oxymethyleneoxy, oxyethyleneoxy, oxy-1,4-butanediyloxy and the like, oxyalkylenearylenealkyleneoxy such as oxymethylenephenylenemethyleneoxy, oxyethylenephenylenemethyleneoxy, oxypropylenephenylenemethyleneoxy, oxyethylenenaphthyleneethyleneoxy and the like, thio, thioalkyleneoxy such as thiomethyleneoxy, thioethylleneoxy and the like, sulfinyldioxy, oxy(alkoxy)phosphinooxy such as oxy(methoxy)phosphinooxy, oxy(ethoxy) phosphinooxy, oxy(butoxy)phosphinooxy and the like, aminocarbonyl, N-alkylaminocarbonyl such as N-methylaminocarbonyl, N-ethylaminocarbonyl, N-butylaminocarbonyl and the like, N-arylaminocarbonyl such as N-phenylaminocarbonyl, N-(3-methylphenyl)aminocarbonyl and the like, aminocarbonylalkyleneoxy such as aminocarbonylmethyleneoxy, aminocarbonyl-1,4-butanediyloxy, N-methylaminocarbonylmethyleneoxy, N-phenylaminocarbonylethyleneoxy and the like, aminocarbonylamino, alkylaminocarbonylamino such as N-methylaminocarbonylamino, N-ethylaminocarbonylamino and the like, di(N-alkylamino)carbonyl such as N-methylaminocarbonyl-N'-methylamino, N-ethylamiocarbonyl-N'-methylamino, N-ethylaminocarbonyl-N'-butylamino and the like, arylaminocarbonylamino such as N-phenylaminocarbonylamino, N-(3-methylphenyl)aminocarbonylamino, N-arylaminocarbonyl-N'-arylamino, such as N-phenylaminocarbonyl-N'-phenylamino, N-alkylaminocarbonyl-N'-arylamino such as N-methylaminocarbonyl-N'-phenylamino and the like, N-arylaminocarbonyl-N'-alkylamino such as N-phenylaminocarbonyl-N'-methylamino or N-methylaminocarbonyl-N'-phenylamino and the like, amino, alkyleneamino such as methyleneamino, 1,4-butanediylamino, 1,5-pentanediylamino, and the like, aryleneamino such as phenyleneamino and the like, N-alkylaminoalkyleneoxy such as N-methylaminomethyleneoxy, N-ethylaminomethyleneoxy and the like, N-arylaminoalkyleneoxy such as N-phenylaminomethyleneoxy, N-phenylaminoethyleneoxy and the like, oxyalkyleneaminoalkyleneoxy such as oxymethyleneaminomethyleneoxy, oxymethyleneaminoethyleneoxy and the like, alkyleneaminocarbonylamino such as methyleneaminocarbonylamino, ethyleneaminocarbonylamino and the like, oxyalkylene(N-alkyl)aminoalkyleneoxy such as oxymethylene(N-methyl)aminomethyleneoxy and the like, alkyleneaminoalkylene such as methyleneaminomethylene, ethyleneaminoethylene and the like, aryleneaminoarylene such as phenyleneaminophenylene and the like, aryleneaminoalkylene such as phenyleneaminomethylene and the like, alkyleneaminoarylene such as methyleneaminophenylene and the like;

wherein C is a hydroxybenzophenone group having the formula

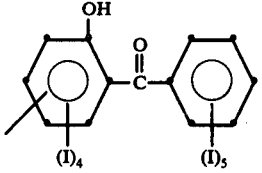

are for example, 2-hydroxybenzophenone, 2,4-dihydroxy-4'-methylbenzophenone, 5-chloro-2,4-dihydroxybenzophenone, 2,3'-dihydroxybenzophenone, 2,5-dihydroxybenzophenone, 4-amino-2-hydroxybenzophenone, 2,2'-dihydroxybenzophenone, 2-hydroxy-4'-methoxybenzophenone, 2-hydroxy-4'-octyloxybenzophenone, 2,2',6,6'-tetrahydroxybenzophenone, 2,2',4-trihydroxybenzophenone, 2,4-dihydroxybenzophenone, 2-hydroxy-4-methoxybenzophenone, 2-hydroxy-4-octyloxybenzophenone.

The heterocyclic compositions can be added to organic compositions which are susceptible to ultraviolet degradation. Such compositions include, for example, polymeric compositions such as polyester fiber and molding compositions, such as polyethylene terephthalate, polymethylene terephthalate and the like; polyolefins such as, for example, high, medium and low density polyethylene, polypropylene, polybutene and the like; polyamides such as N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The multichromophoric compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel multichromophoric ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1

Preparation of 4-{2-[4-(2H-benzotriazol-2-yl)-2,6-xylyloxy)-ethoxy}-2-hydroxybenzophenone (1) can be prepared by the following procedure:

o-Nitroaniline (0.5 mole) was diazotized in the usual manner with concentrated hydrochloric acid (120 ml.) and sodium nitrite (0.5 mole). The clear diazonium solution was added slowly to a cold solution (0–5° C.) of 2,6-dimethylphenol (0.5 mole) in 450 ml. of 10% sodium hydroxide. The mixture was stirred for 1 hour and Compound A filtered out (80% yield). One-tenth mole of Compound A was dissolved in 100 ml. of 2N NaOH. Zinc dust (30 g.) and sodium hydroxide (50 ml. of a 25% solution) were added slowly to the well-stirred solution. The mixture was then cooled to <30° C. and acidified with concentrated hydrochloric acid. After stirring for 2 hours, the precipitate was filtered. Compound B was recrystallized from toluene (m.p. 185°–188° C., 60% yield). A mixture of the sodium salt of Compound B (0.01 mole) and 4-(2-bromoethoxy)-2-hydroxybenzophenone (0.01 mole) in 250 ml. of ethanol was refluxed for 15 hours. The product, C, was crystallized from ethanol after removal of sodium bromide by filtration. (Yield: 50%, m.p. 135°–138° C.). Anal. Calcd. for $C_{29}H_{25}N_3O_4$: C, 72.65; H, 5.22; N, 8.77. Found C, 71.73; H, 5.40; N, 8.08.

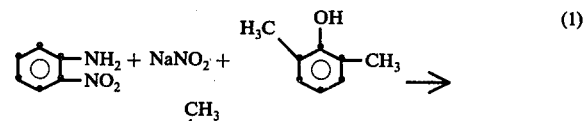

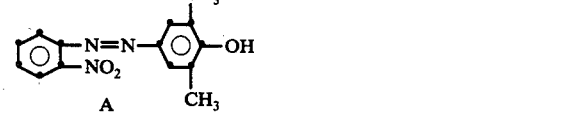

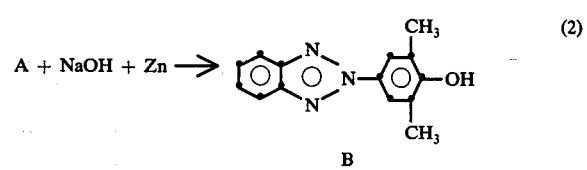

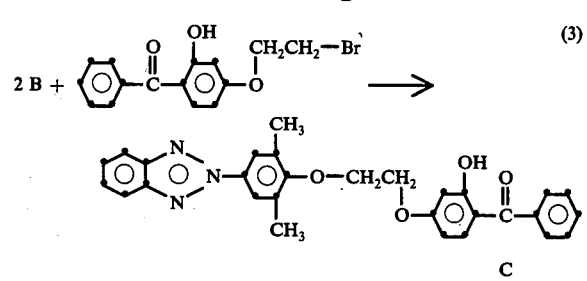

Other novel multichromophoric compounds can be prepared by substituting of other benzotriazoles for 4-(2H-benzotriazol-2-yl)-2,6-dimethylphenol, such as 4-(5-chloro-2H-benzotriazol-2-yl)-2,6-dimethylphenol, 4-(5-chloro-2H-benzotriazol-2-yl)phenol, 4-(5-methyl-2H-benzotriazol-2-yl)-2,6-dimethylphenol, 4-(5-methyl-2H-benzotriazol-2-yl)-2-methylphenol, 4-(5-chloro-2H-benzotriazol-2-yl)-2-methylphenol, 4-(2H-benzotriazol-2-yl)-2-methylphenol, 4-(2H-benzotriazol-2-yl)-2-chlorophenol, 4-(5-chloro-2H-benzotriazol-2-yl)-2-chlorophenol, 4-(5-methyl-2H-benzotriazol-2-yl)-2-chlorophenol, 4-(2H-benzotriazol-2-yl)-2,6-dimethoxyphenol, 4-(5-chloro-2H-benzotriazol-2-yl)-2,6-dimethoxyphenol, 4-(5-methyl-2H-benzotriazol-2-yl)-2,6-dimethoxyphenol, 4-(2H-benzotriazol-2-yl)-2-methoxyphenol, 4-(5-chloro-2H-benzotriazol-2-yl)-2-methoxyphenol, and 4-(5-methyl-2H-benzotriazol-2-yl)-2-methoxyphenol.

Also, other multichromophoric compounds can be prepared by substituting other hydroxybenzophenones for 4-(2-bromoethoxy)-2-hydroxybenzophenone such as 4'-(2-bromoethoxy)-2-hydroxybenzophenone, 4-(2-bromoethoxy)-2,2'-dihydroxybenzophenone, 4'-(2-bromopropoxy)-2,2'-dihydroxybenzophenone and 4-(3-bromopropoxy)-2,2'-dihydroxybenzophenone, 4-(3-bromopropoxy)-2-hydroxybenzophenone and 4-(2-bromopropoxy)-2-hydroxybenzophenone.

This example hereinabove shows the B linking group as an oxyalkyleneoxy group. Other B linking groups can be provided as known in the art as for example:
1. an oxycarbonylalkyleneoxy by esterification of an acid or acid chloride with an alcohol or phenol in alkaline medium;
2. an oxycarbonyloxy by the reaction of phosgene with alcohol or phenol in alkaline medium;
3. an alkyleneoxy by the reaction of halide with alkali salt of alcohol or phenol;
4. an alkyleneoxyalkyleneoxy by the reaction of halide with alkali salt of alcohol or phenol;
5. a sulfinyldioxy by the reaction of thionyl chloride with alcohol or phenol in alkaline solution;
6. a thio by the reaction of a sodium sulfide with a halide;
7. an oxy(alkoxy)phosphinooxy by the reaction of a dichlorophosphite with phenol in the presence of a base;
8. an N-alkyl or N-arylaminocarbonyl by the reaction of an acid chloride with an amine;
9. an N-alkyl or N-arylaminocarbonylalkoxy by the reaction of an acid chloride with an amine;
10. an N-alkyl or N-arylaminocarbonylamino by the reaction of phosgene with an amine;
11. an N-alkyl or N-arylaminoalkylene by the reaction of an alkyl halide with an amine;
12. an N-alkyl or N-arylaminoalkyleneoxy by the reaction of an oxyalkyl halide with an amine.

EXAMPLE 2

4-{2-[4-(2H-Benzotriazol-2-yl)phenoxy]ethoxy}-2-hydroxybenzophenone (II) can be similarly prepared by the procedure of Example 1 as follows:

o-Nitroaniline (138 g.) was diazotized in the usual manner with concentrated hydrochloric acid (400 ml.), water (200 ml.) and sodium nitrite (72 g.). The clear diazonium solution was added slowly to a cold solution of phenol (94 g.) in 900 ml. of 10% sodium hydroxide. The mixture was stirred for 1 hour and filtered, yielding 136 g. (56%) of the diazo compound (m.p. 154°–158° C.). This product was dissolved in 650 ml. of 2N sodium hydroxide solution. Zinc dust (130 g.) and sodium hydroxide (100 ml. of a 25% solution) were added slowly to the well-stirred solution. The mixture was cooled to <30° C. and acidified with concentrated hydrochloric acid. After stirring for 2 hours, the precipitate was filtered. The precipitate was taken up in 1 liter of hot ethanol, solution filtered, cooled and product, p-(2H-benzotriazol-2-yl)phenol, filtered out (m.p. 216°–218° C.). A well-stirred mixture of p-(2H-benzotriazol-2-yl)phenol (0.01 mole), 4-(2-bromoethoxy)-2-hydroxybenzophenone (0.01 mole), potassium carbonate (0.01 mole) and 200 ml. of methyl ethylketone were refluxed for 16 hours. The reaction mixture was filtered and the solvent removed on a steam bath. The precipitate, II, was recrystallized from toluene, m.p. 172°–176° C., 90°–95° pure.

Anal. calcd. for $C_{27}H_{21}N_3O_4$: C, 71.83; H, 4.69; N, 9.31. Found: C, 68.86; H, 4.75; N, 8.56.

EXAMPLE 3

[p-(2H-Benzotriazol-2-yl)phenyl](4-benzoyl-3-hydroxyphenyl)acetate (III) can be prepared as follows:

p-(2H-Benzotriazol-2-yl)phenol (0.01 mole) (prepared as in Example 2), 4-benzoyl-3-hydroxyphenyl acetic acid (0.01 mole), boric acid (0.031 g.), sulfuric acid (0.3 ml.) and xylene (200 ml.) were stirred and refluxed overnight (the water was azeotroped out of the reaction as formed). The mixture was cooled and filtered. The product, III, was recrystallized from toluene (m.p. 141°).

Anal. calcd. for $C_{27}H_{19}N_3O_5$: C, 67.67; H, 4.11; N, 9.03. Found. C, 66.91; H, 4.52; N, 10.52.

EXAMPLE 4

The ultraviolet stabilization provided by the heterocyclic compound of the present invention is shown for poly(tetramethylene terephthalate) in Table 1.

A dry mixture of the stabilizer and granulated poly(tetramethylene terephthalate) was extruded into 1/16-inch diameter rods, pelletized and injection molded into 2½ ×  × 1/16-inch flat bars; these flat bars were exposed to a 280–700 nm. mercury lamp source until a flatwise impact strength of less than 6 was obtained (initial values were all >17).

The test results are summarized in Table 1.

Table 1

| | FWIS (Flatwise Impact Strength) | |
|---|---|---|
| Compound (0.5%) | Initial | 500 hr. |
| None | 17 | 1 |
| I | 19 | 20 |
| II | 19 | 20 |
| III | 19 | 20 |

Effectiveness of Ultraviolet Stabilizers in Poly(tetramethylene terephthalate)

These multichromophoric compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:
1. An organic composition susceptible to ultraviolet light degradation stabilized against such degradation with a stabilizing amount of at least one multichromophoric compound having the formula:

A—B—C wherein
A is a group having the structure

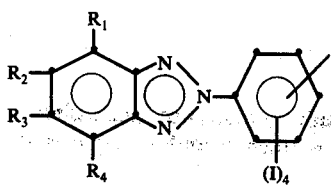

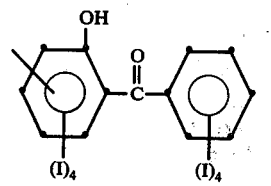

wherein $R_1$, $R_2$, $R_3$ and $R_4$ are hydrogen, chloro, bromo, lower alkyl, substituted lower alkyl, cycloalkyl, substituted cycloalkyl, aryl, substituted aryl, lower alkylaryl, aryl-substituted-aryl, alkoxy, substituted amino, cyano, carboxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;

I is the same as $R_1$, $R_2$, $R_3$ and $R_4$ and is present on all positions of the benzenoid ring, except the carbon atom attached to the heterocyclic ring and the carbon atom attached to the B group connecting the heterocyclic aromatic A group with the aromatic C group, wherein B is a group connecting A and C and can be alkylene, arylene, carbonyloxy, oxycarbonylalkyleneoxy, oxycarbonyl, alkyleneoxycarbonyloxy, oxyalkylenecarbonyloxy, oxycarbonyloxy, alkyleneoxy, oxyalkylene, alkyleneoxyalkyleneoxy, oxyalkylenearylenealkyleneoxy, thio, thioalkyleneoxy, sulfinyldioxy, oxy(alkoxy)phosphinooxy, aminocarbonyl, N-alkylaminocarbonyl, N-arylaminocarbonyl, aminocarbonylalkyleneoxy, N-alkylaminocarbonylalkyleneoxy, N-arylaminocarbonylalkyleneoxy, aminocarbonylamino, N-alkylaminocarbonylamino, N,N-dialkylaminocarbonyl, N-arylaminocarbonyl, N-alkylaminocarbonyl, N,N-diarylaminocarbonyl, amino, N-alkylamino, N-arylamino, N-alkylaminoalkyleneoxy, N-arylaminoalkyleneoxy, oxyalkyleneoxy, oxyaryleneoxy, alkyleneaminoalkylene, aryleneaminoarylene, aryleneaminoalkylene and alkyleneaminoarylene; and wherein C is a hydroxybenzophenone group having the formula where I is the same substituent as listed above and is present in all positions of the benzoid rings except the carbon atom attached to the B group connecting the A and C moieties, said B connecting group is attached to the benzoid ring in the ortho, meta or para position from the keto group of the benzophenone, and said I substituents can all be one of the substituents listed above or different listed substituents.

2. An organic composition according to claim 1 wherein said multichromic compound has the formula:

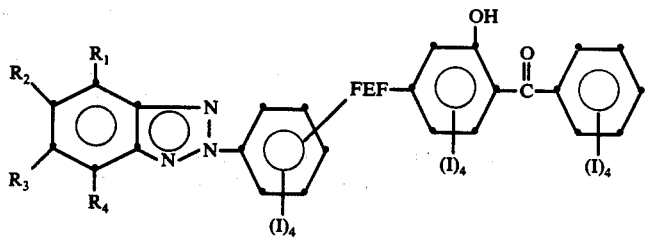

wherein

E is a member selected from the group consisting of a branched or unbranched alkylene group containing 1 to 8 carbon atoms, a carbonyl alkylene group containing 2 to 9 carbon atoms, an alkylene carbonyl group containing 2 to 9 carbon atoms, an alkylene arylene alkylene group containing 8 to 18 carbon atoms, and F is oxygen, nitrogen or sulfur;

$R_1$, $R_2$, $R_3$ and $R_4$ are hydrogen, chloro, bromo, lower alkyl, substituted lower alkyl, cycloalkyl, substituted cycloalkyl, aryl, substituted aryl, lower alkylaryl, alkoxy, amino, substituted amino, cyano, carboxy and the substituents $R_1$ and $R_2$, and $R_3$, $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;

I is the same as $R_1$, $R_2$, $R_3$ and $R_4$ and is present on all positions of the benzenoid ring, except the carbon atom attached to the FEF substituent, said I substituents can all be one of the substituents listed above or different listed substituents.

3. An organic composition according to claim 2 wherein said multichromophoric compound has the formula:

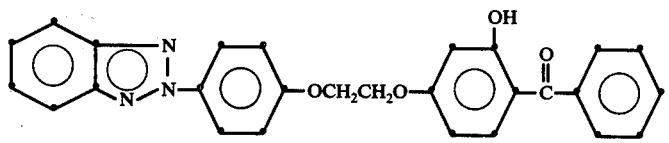

4. An organic composition according to claim 2 wherein said multichromophoric compound has the formula:

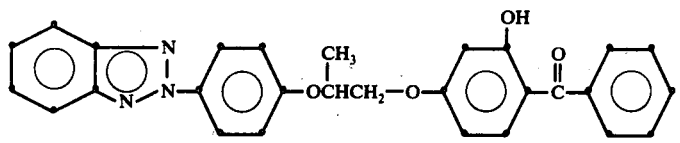

5. An organic composition according to claim 2 wherein said multichromophoric compound has the formula:

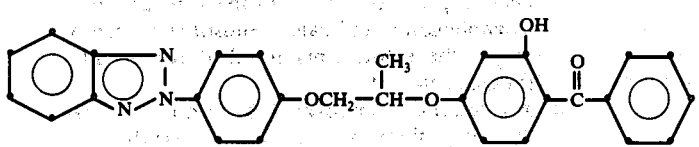

6. An organic composition according to claim 2 wherein said multichromophoric compound has the formula:

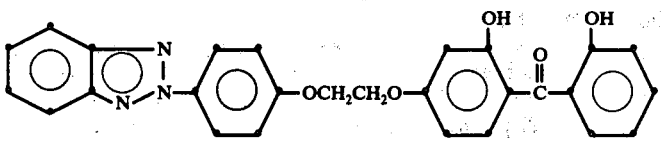

7. An organic composition according to claim 2 wherein said multichromophoric compound has the formula:

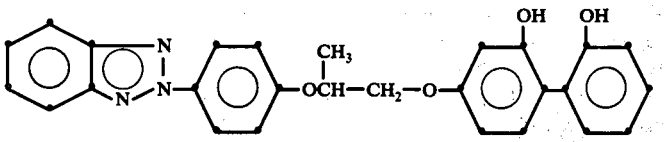

8. An organic composition according to claim 2 wherein said multichromophoric compound has the formula:

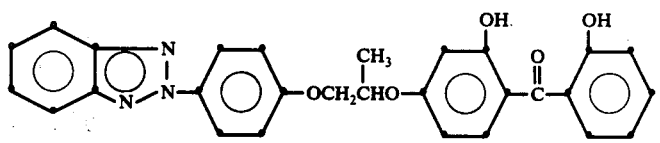

9. An organic composition according to claim 2 wherein said multichromophoric compound has the formula:

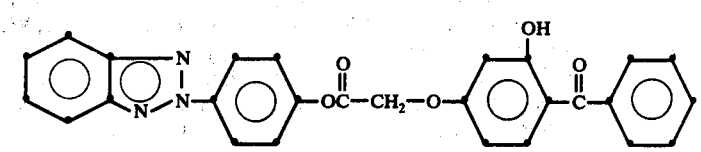

10. An organic composition according to claim 2 wherein said multichromophoric compound has the formula:

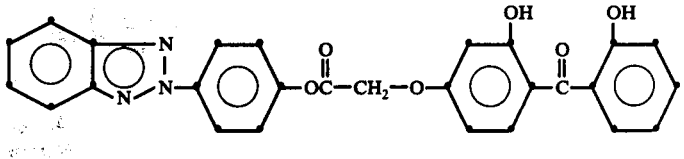

11. An organic composition according to claim 2 wherein said multichromophoric compound has the formula:

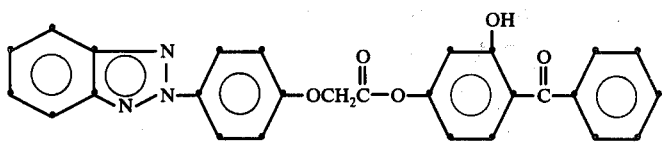

12. An organic composition according to claim 2 wherein said multichromophoric compound has the formula:

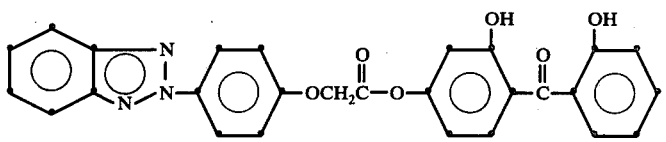

13. An organic composition according to claim 2 wherein said multichromophoric compound has the formula:

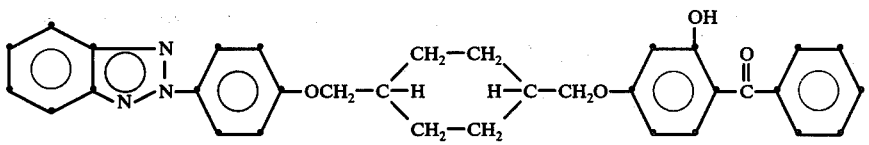

14. An organic composition according to claim 2 wherein said multichromophoric compound has the formula:

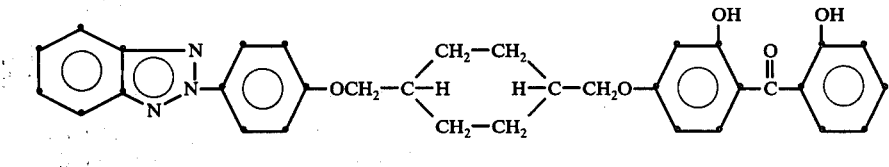

15. An organic composition according to claim 2 wherein said multichromophoric compound has the formula:

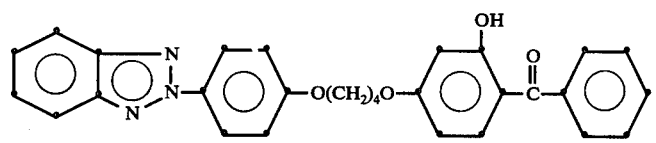

16. An organic composition according to claim 2 wherein said multichromophoric compound has the formula:

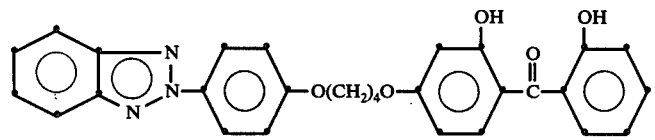

17. An organic composition according to claim 2 wherein said multichromophoric compound has the formula:

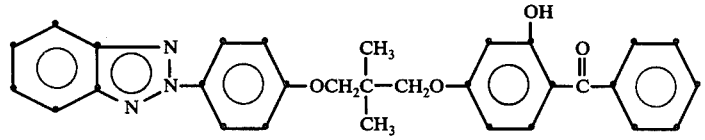

18. An organic composition according to claim 2 wherein said multichromophoric compound has the formula:

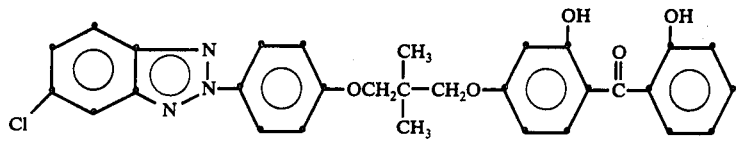

19. An organic composition according to claim 2 wherein said multichromophoric compound has the formula:

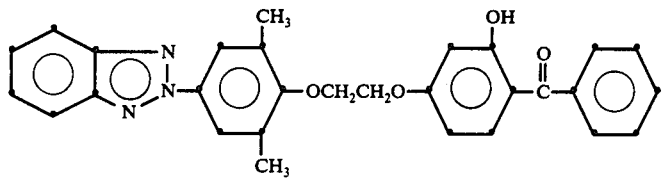

20. An organic composition according to claim 2 wherein said multichromophoric compound has the formula:

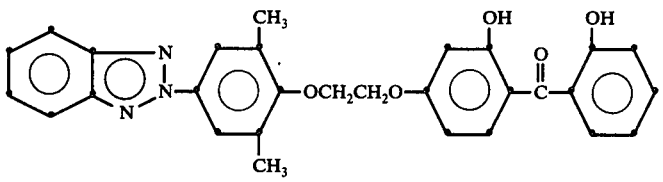

21. An organic composition according to claim 2 wherein said multichromophoric compound has the formula:

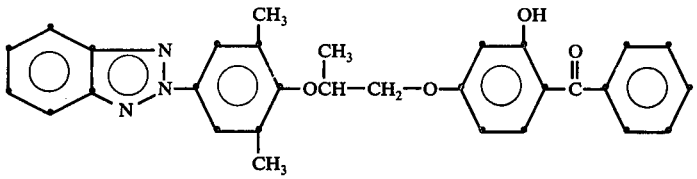

22. An organic composition according to claim 2 wherein said multichromophoric compound has the formula:

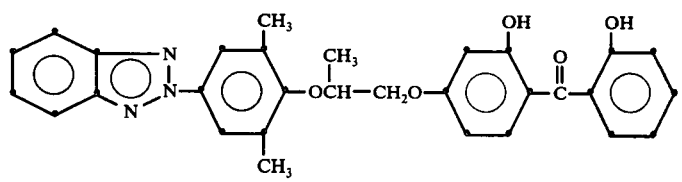

23. An organic composition according to claim 2 wherein said multichromophoric compound has the formula:

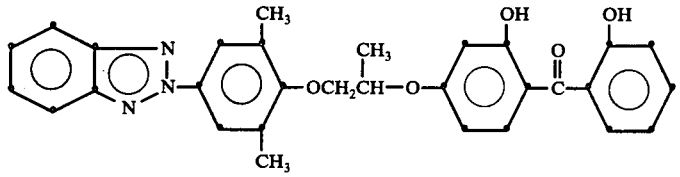

24. An organic composition according to claim 2 wherein said multichromophoric compound has the formula:

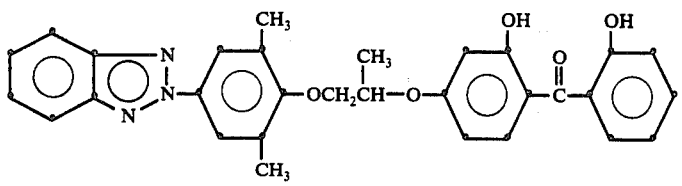

25. An organic composition according to claim 2 wherein said multichromophoric compound has the formula:

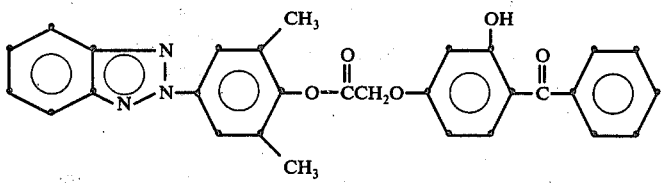

26. An organic composition according to claim 2 wherein said multichromophoric compound has the formula:

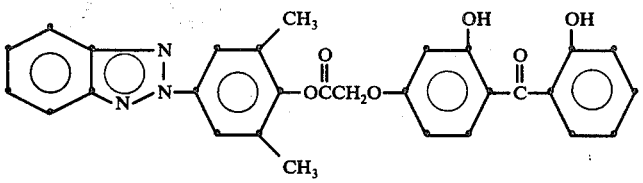

27. An organic composition according to claim 2 wherein said multichromophoric compound has the formula:

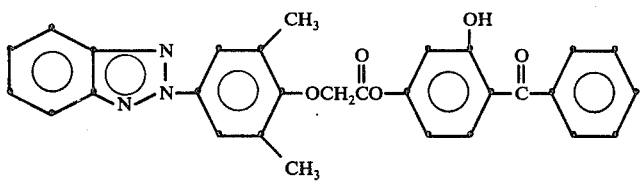

28. An organic composition according to claim 2 wherein said multichromophoric compound has the formula:

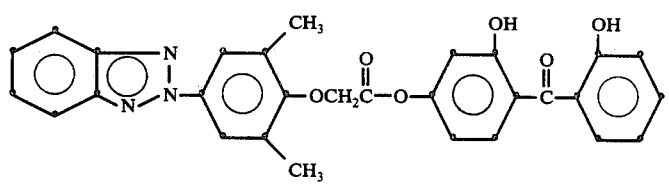

29. An organic composition according to claim 2 wherein said multichromophoric compound has the formula:

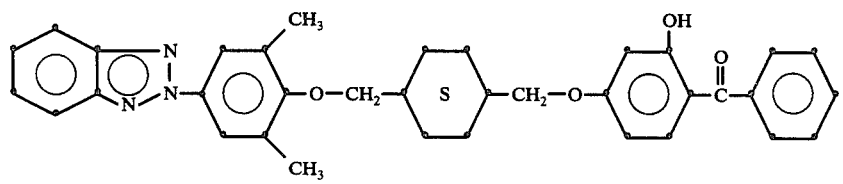

30. An organic composition according to claim 2 wherein said multichromophoric compound has the formula:

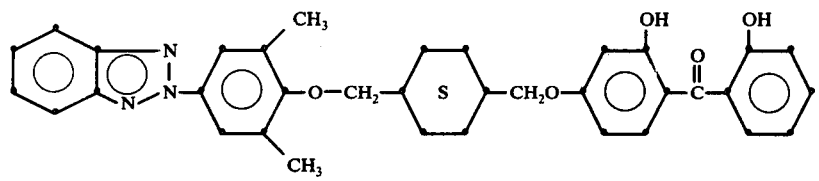

31. An organic composition according to claim 2 wherein said multichromophoric compound has the formula:

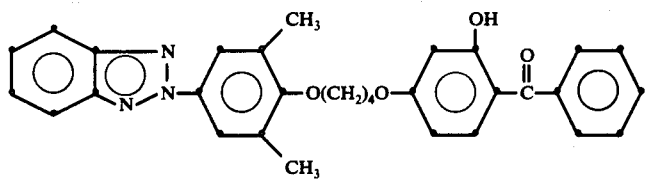

32. An organic composition according to claim 2 wherein said multichromophoric compound has the formula:

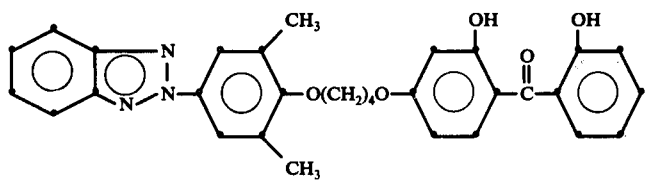

33. An organic composition according to claim 2 wherein said multichromophoric compound has the formula:

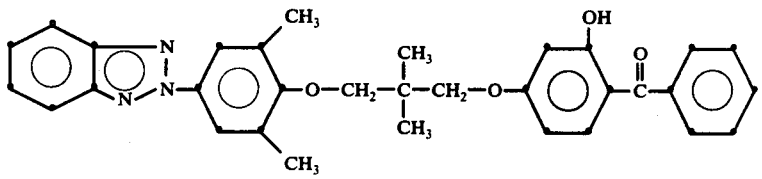

34. An organic composition according to claim 2 wherein said multichromophoric compound has the formula:

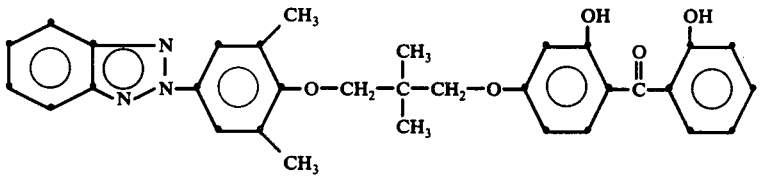

* * * * *

UNITED STATES PATENT OFFICE
CERTIFICATE OF CORRECTION

Patent No. 4,073,745  Dated February 14, 1978

Inventor(s) Richard H.S. Wang and Joseph S. Zannucci

It is certified that error appears in the above-identified patent and that said Letters Patent are hereby corrected as shown below:

Column 10, line 45, after "$R_1$ and $R_2$," insert ---$R_2$---.

Column 16, Claim 23, delete the formula and insert therefor

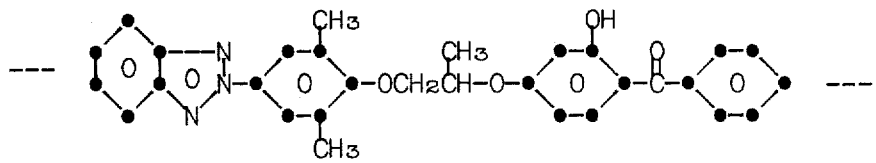

Column 19, Claim 31, delete the formula and insert therefor

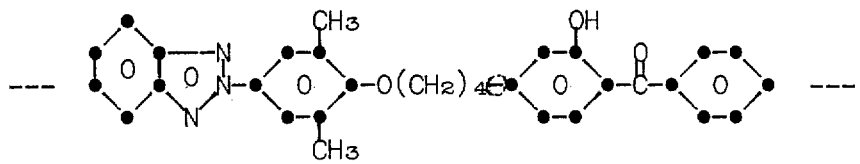

Signed and Sealed this

Twenty-seventh Day of June 1978

[SEAL]

Attest:

RUTH C. MASON
Attesting Officer

DONALD W. BANNER
Commissioner of Patents and Trademarks